(12) United States Patent
Canada et al.

(10) Patent No.: US 8,563,447 B2
(45) Date of Patent: Oct. 22, 2013

(54) SILVER-CONTAINING WOUND CARE DEVICE

(75) Inventors: T. Andrew Canada, Campobello, SC (US); Robert L. Schuette, Boiling Springs, SC (US); Raymond C. Sturm, Spartanburg, SC (US); Kenneth M. Wiencek, Inman, SC (US); Jason L. Kreider, Boiling Springs, SC (US)

(73) Assignee: Milliken & Company, Spartanburg, SC (US)

( * ) Notice: Subject to any disclaimer, the term of this patent is extended or adjusted under 35 U.S.C. 154(b) by 1313 days.

(21) Appl. No.: 10/640,918

(22) Filed: Aug. 14, 2003

(65) Prior Publication Data

US 2005/0037680 A1  Feb. 17, 2005

(51) Int. Cl.
*B32B 27/04* (2006.01)

(52) U.S. Cl.
USPC ...... 442/123; 424/78.1; 427/125; 106/170.28

(58) Field of Classification Search
USPC .................. 428/376, 375; 442/123; 424/78.1; 427/125; 106/170.28
See application file for complete search history.

(56) References Cited

U.S. PATENT DOCUMENTS

| | | | | |
|---|---|---|---|---|
| 2,955,961 | A | * | 10/1960 | Koller ............................. 442/93 |
| 3,844,862 | A | * | 10/1974 | Sauer et al. ...................... 156/78 |
| 3,930,000 | A | | 12/1975 | Margraf ........................... 424/245 |
| 4,341,207 | A | * | 7/1982 | Steer et al. ........................ 602/56 |
| 4,728,323 | A | | 3/1988 | Matson ........................... 604/304 |
| 5,019,096 | A | | 5/1991 | Fox, Jr. et al. ..................... 623/1 |
| 5,147,338 | A | | 9/1992 | Lang et al. ....................... 604/304 |
| 5,161,686 | A | * | 11/1992 | Weber et al. .................... 206/440 |
| 5,296,518 | A | | 3/1994 | Grasel et al. .................... 521/176 |
| 5,409,472 | A | | 4/1995 | Rawlings et al. ............. 604/307 |
| 5,432,000 | A | * | 7/1995 | Young et al. .................... 428/372 |
| 5,571,079 | A | | 11/1996 | Bello et al. ...................... 602/46 |
| 5,607,683 | A | | 3/1997 | Capelli ........................... 424/405 |
| 5,662,913 | A | | 9/1997 | Capelli ........................... 424/405 |
| 5,744,151 | A | | 4/1998 | Capelli ........................... 424/405 |
| 5,782,787 | A | | 7/1998 | Webster ........................... 602/46 |
| 5,810,755 | A | | 9/1998 | LeVeen et al. ................... 602/48 |
| 5,899,785 | A | | 5/1999 | Groten et al. .................. 442/334 |
| 5,914,125 | A | | 6/1999 | Andrews et al. ............... 424/443 |
| 5,968,597 | A | * | 10/1999 | Vogt et al. ..................... 427/377 |
| 5,970,583 | A | | 10/1999 | Groten et al. .................... 19/296 |
| 5,973,221 | A | | 10/1999 | Collyer et al. .................. 602/46 |
| 6,019,996 | A | | 2/2000 | Cheong .......................... 424/445 |
| 6,071,447 | A | | 6/2000 | Bootman et al. ................. 264/54 |
| 6,087,549 | A | | 7/2000 | Flick ................................ 602/41 |
| 6,093,414 | A | | 7/2000 | Capelli ........................... 424/405 |
| 6,143,318 | A | | 11/2000 | Gilchrist et al. ............... 424/446 |
| 6,153,215 | A | | 11/2000 | Samuelsen et al. ........... 424/448 |
| 6,160,196 | A | | 12/2000 | Knieler et al. ................... 602/48 |
| 6,326,410 | B1 | | 12/2001 | Cheong ........................... 521/67 |
| 6,333,093 | B1 | | 12/2001 | Burrell et al. .................. 428/194 |
| 6,399,091 | B1 | | 6/2002 | Berthold et al. ............... 424/443 |
| 6,468,521 | B1 | | 10/2002 | Pedersen et al. ........... 424/78.17 |
| 6,548,727 | B1 | | 4/2003 | Swenson ......................... 602/41 |
| 6,584,668 | B2 | | 7/2003 | Green et al. .................. 29/527.2 |
| 6,641,829 | B1 | | 11/2003 | Green et al. ................... 424/405 |
| 7,118,761 | B2 | * | 10/2006 | Canada et al. ................ 424/445 |
| 2002/0146957 | A1 | * | 10/2002 | Fuller et al. .................... 442/409 |
| 2002/0172709 | A1 | | 11/2002 | Nielsen et al. ................ 424/445 |
| 2002/0187175 | A1 | | 12/2002 | Petrea et al. ................... 424/404 |
| 2002/0192386 | A1 | * | 12/2002 | Green et al. ................... 427/402 |
| 2003/0021832 | A1 | | 1/2003 | Scherr ........................... 424/445 |
| 2004/0106342 | A1 | * | 6/2004 | Sturm et al. .................... 442/117 |
| 2004/0214490 | A1 | * | 10/2004 | Kreider et al. .................. 442/59 |

FOREIGN PATENT DOCUMENTS

| | | | | |
|---|---|---|---|---|
| GB | 2 093 703 | A | 2/1982 | ............. A61F 13/00 |
| WO | WO 02/62403 | A1 | 2/2002 | ............. A61L 15/44 |
| WO | WO 02/78755 | A2 | 3/2002 | ............. A61L 15/44 |
| WO | WO 02/36866 | A1 | 5/2002 | ............. D01F 9/04 |
| WO | WO 03/043553 | A1 | 5/2003 | ............. A61F 13/02 |

OTHER PUBLICATIONS

Abstract: JP9078430A2—Production of Antibacterial Long-Fiber Non-Woven Fabric, Filed: Sep. 11, 1995, Country: JP, Class: D04H 3, Sub-Class: 00.

* cited by examiner

*Primary Examiner* — Ali Soroush
(74) *Attorney, Agent, or Firm* — Brenda D. Wentz

(57) ABSTRACT

Wound care devices having a topically applied silver-based antimicrobial finish are provided. The finish comprises at least one silver ion-containing compound and at least one binder compound. The finish may be applied to a target substrate, such as a fiber, fabric, film, foam, hydrogel, or hydrocolloid to provide a single layer antimicrobial wound care device. Alternatively, a silver-containing layer may be combined with one or more additional layers of target substrate to provide a composite antimicrobial wound care device. The device may also contain an odor-absorbing component capable of reducing or eliminating odors that are inherently associated with infectious wounds. Also provided is a method for making the wound care device and a composition of matter comprising the silver-based antimicrobial finish.

6 Claims, 4 Drawing Sheets

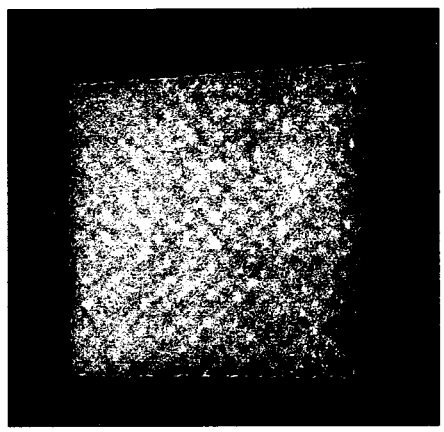 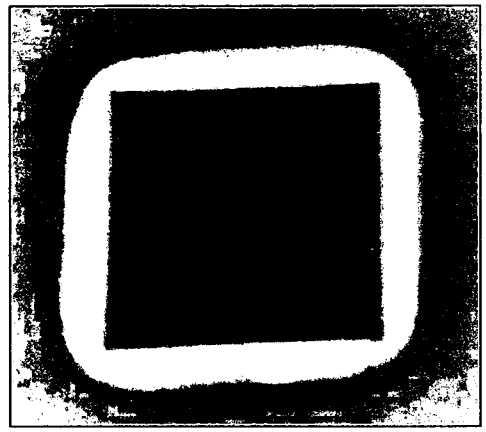
CONTROL  EXAMPLE 1
FIG. −1−

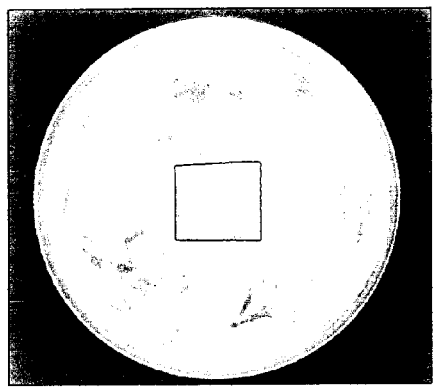
CONTROL
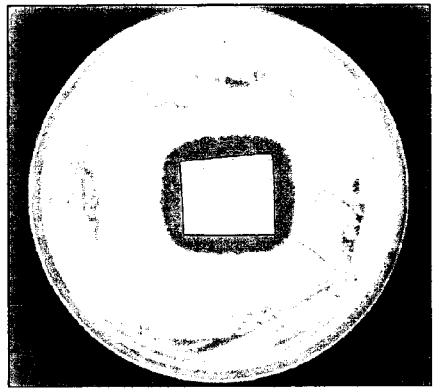
EXAMPLE 1
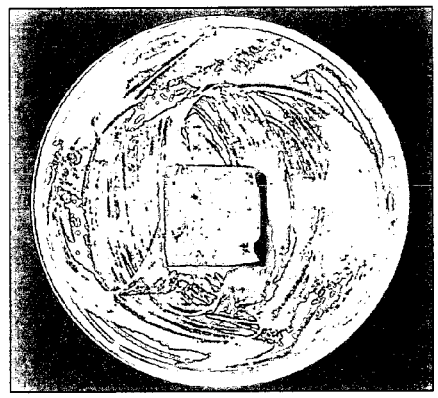
COMPARATIVE
EXAMPLE A
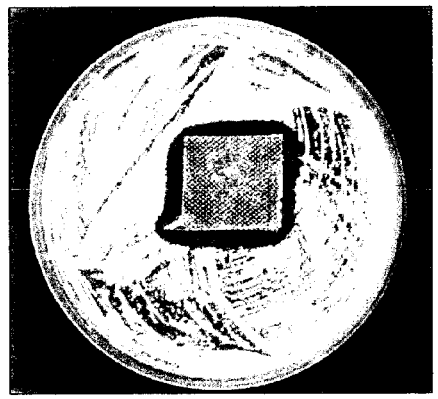
COMPARATIVE
EXAMPLE B
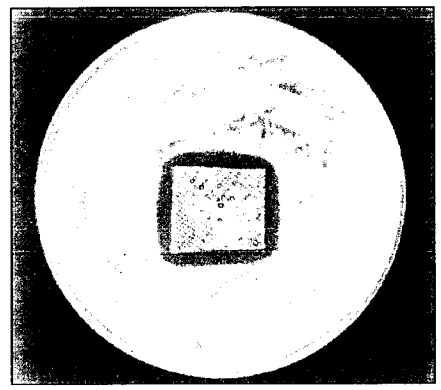
COMPARATIVE
EXAMPLE C
*FIG. —2—*

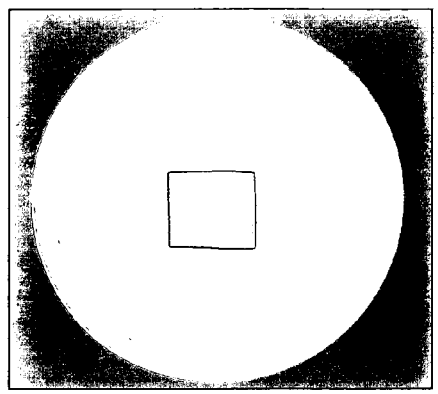
CONTROL
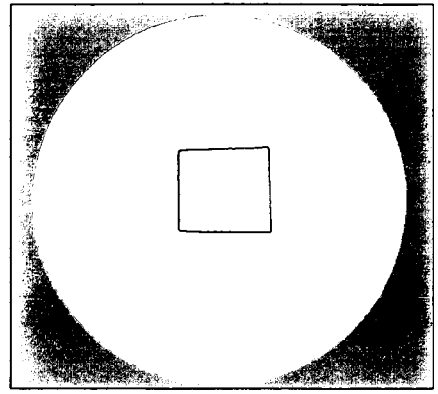
EXAMPLE 1
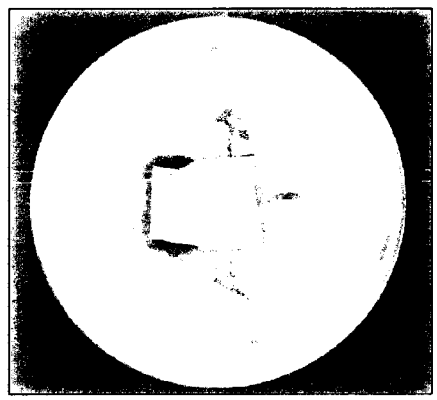
COMPARATIVE
EXAMPLE A
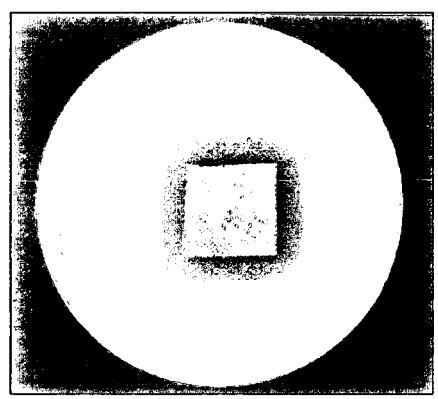
COMPARATIVE
EXAMPLE B
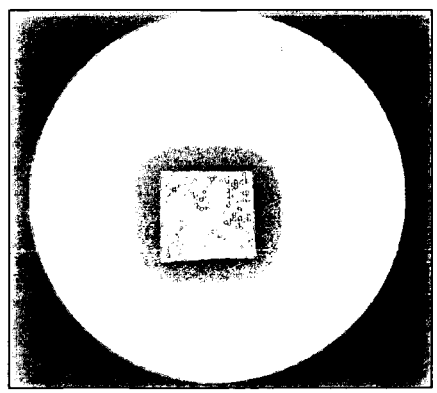
COMPARATIVE
EXAMPLE C
*FIG. −3−*

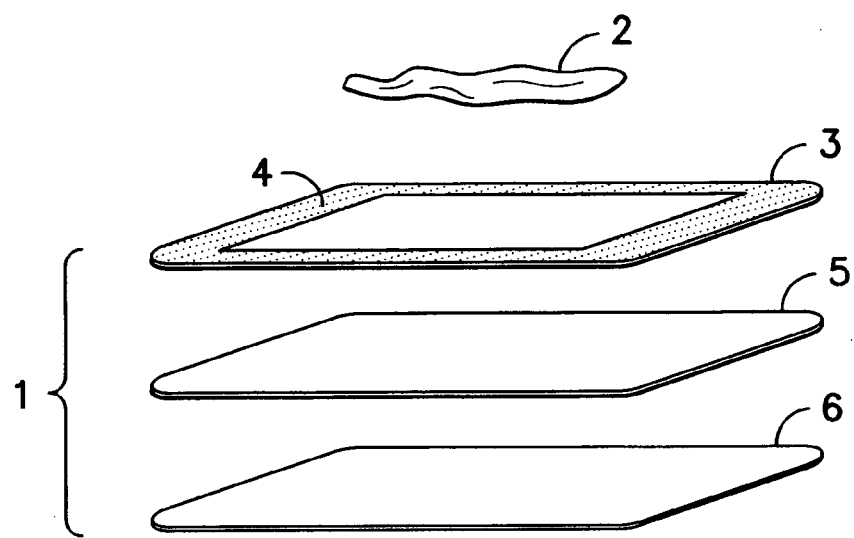
FIG. -4-
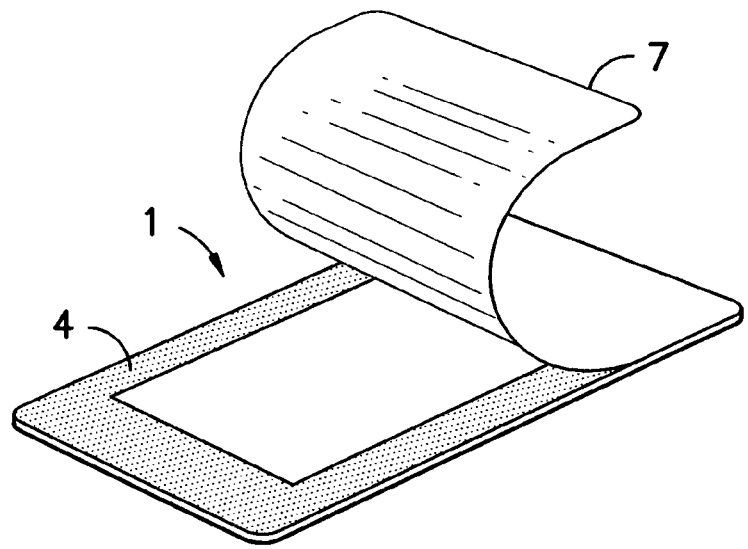
FIG. -5-

SILVER-CONTAINING WOUND CARE DEVICE

FIELD OF THE INVENTION

This invention relates to wound care devices having a topically applied silver-based antimicrobial finish. The finish may be applied to a target substrate to provide a single layer antimicrobial wound care device. Alternatively, a silver-containing layer may be combined with one or more additional layers of the target substrate to provide a composite antimicrobial wound care device. The device may also contain an odor-absorbing component capable of reducing or eliminating odors that are inherently associated with infectious wounds. In one potentially preferred embodiment, a silver-based antimicrobial finish is topically applied to a nonwoven fabric comprised of multi-component fibers that are at least partially split into their microdenier components. Such structure provides greater surface area onto which the silver ions may adhere, thus increasing the amount of surface available silver that is present on the wound care device for promoting healing of the wound. The structure further allows the fabric to be highly absorbent, despite being made of synthetic materials, which is desirable for drawing excess moisture, or exudate, away from the wound.

BACKGROUND OF THE INVENTION

Silver-containing microbicides have been incorporated into wound care devices and are rapidly gaining acceptance in the medical industry as a safe, effective means of controlling microbial growth. It has long been recognized that silver plays an important role in promoting wound healing and in preventing infection of the wound. For example, U.S. Pat. No. 3,930,000 discloses the use of a silver zinc allantoinate cream for killing bacteria and fungi associated with burn wounds, and Japanese Abstract 09078430A discloses the incorporation of zirconium phosphate carrying silver into a thermoplastic olefin-based polymer melt for the extrusion of a synthetic antimicrobial fiber. Thus, it is known that placing surface available silver in contact with a wound allows the silver to enter the wound and become ingested by undesirable bacteria and fungi that grow and prosper in the warm, moist environment of the wound site. Once ingestion occurs, the silver kills the bacteria and fungi, which aids in preventing infection of the wound and promotes the healing process.

In addition to containing silver, it is important that wound care devices are capable of moisture management during the various phases of wound healing. For example, immediately after an injury occurs, it is important that the wound care device readily absorbs exudate from the wound site to promote the healing process and help prevent infection. Excess liquid from the wound site, especially if the liquid is allowed to pool, will generally foster a warm, moist environment ideal for microbial growth. During the next phase of granulation, when new cells are generated, it is desirable that the wound care device provides a balanced moist environment. More specifically, to prevent the wound care device from undesirably adhering to the wound site, it is advantageous to design the device so that it absorbs excess exudate, but does not dry out the wound completely thereby causing the device to stick to the new layer of cells that have formed. The final stage of healing typically involves the formation of scar tissue. During this phase, it is important that the wound care device allows the wound to maintain some moisture. Thus, a wound care device having a high degree of breathability is desirable for balancing the exudate absorption capabilities of the device during the various phases of healing.

With the potential for microbial growth at the wound site, another desirable feature of a wound care device is that it absorbs odors emitted by the wound. Especially in chronic, slow-healing wounds, when the application of the wound care device is required for an extended period of time, the lack of oxygen to the wound site may lead to additional bacterial and/or fungal growth. This growth, quite often, leads to infection of the wound and the creation of undesirable odors. Also, in many instances, it is desirable to limit the frequency of changing the wound care device, for instance, in order to not disturb the new cell growth during the healing process. As a result of less frequent changing, the wound care device may develop unwanted odor from association with the wound. Accordingly, the inclusion of an odor receiving agent or layer within or on the wound care device is advantageous.

Furthermore, it is readily known that silver-ion antimicrobial agents, such as ion-exchange compounds like zirconium phosphates, glasses, and/or zeolites, are generally susceptible to discoloration and, due to the solid nature thereof, have a tendency to discolor the substrate in which they are incorporated. More specifically, excess silver ions can combine with available anions to form colored, precipitated salts. Many of these silver salts can darken upon exposure to light as a result of the photo reduction of silver ion to silver metal. This is especially problematic in the medical industry, and specifically in wound care devices, where examination of the wound site as well as the bandage or dressing covering the wound, is an important indicator of the effectiveness of the treatment administered for a particular wound. As such, evidence of discoloration on the wound care device may indicate infection at a wound site. Alternatively, it may be completely unrelated to the status of the wound site and may, instead, be present as a by-product of the degradation of silver ions contained within or on the wound care device itself. Thus, it is important to those in the medical industry that the wound care device itself does not become discolored merely because silver ions are undergoing reduction, which can lead to confusion as to the effectiveness of the treatment being administered to the wound. Accordingly, a stable silver-containing antimicrobial finish on a wound care device is most desirable.

There have been various attempts by others to create wound care devices to address all of the above-identified concerns. In many wound care devices, the microbicide is present throughout the entire cross section of the device. For example, such microbicides have been adapted for incorporation within melt-spun synthetic fibers, as taught within Japanese Abstract 09078430A, in order to provide certain fabrics that selectively and inherently exhibit antimicrobial characteristics. However, such melt-spun fibers are expensive to produce due to the large amount of silver-based compound required to provide sufficient antimicrobial activity, especially in light of the migratory characteristics of the compound from within the fiber itself to its surface. As such, when these silver-containing fibers are combined to form a wound care device, the silver located on the interior of the fiber may never reach the wound site during the useful life of the device to provide any advantage to the healing process. Thus, this provides an inefficient and expensive use of silver in wound care devices, and it is even likely that the amount of silver present on the surface of the fibers is an inadequate amount for promoting the healing process.

Yet another product available on the market is a silver-containing, open-cell foam produced by adding silver to the polymer matrix prior to formation of the foam. The resulting product has silver throughout the entire structure. Generally speaking, the silver in the center of the foam product will never come in contact with the wound site to provide beneficial antimicrobial properties to the wound. Even if the silver Is capable of migrating to the surface of the foam, the frequency with which wound care devices are changed would most likely prevent the silver from achieving any antimicrobial effect on the wound site. Accordingly, much of the silver is used simply to prevent growth of microbes in the bandage itself and is not useful in the treatment of the wound.

Others have attempted to provide composite, multi-layered wound care devices which would achieve all of the desired characteristics described herein. One example includes a multi-layer wound care device comprised of 3 layers—a layer of polyethylene film, a middle layer of rayon/polyester blend nonwoven fabric, and a second layer of film. Nanocrystalline silver particles are deposited onto one or more of the film layers to provide an antimicrobial wound care device. However, this technology generally fails to impart desirable controlled release of silver from the device and the device itself exhibits an undesirable discoloration. Typically, this product will initially release, or dump, large amounts of silver from the wound care device, often in the form of silver flakes which enter the wound bed and lead to irritation of the wound.

Another product available to consumers is a highly porous, silver impregnated charcoal cloth sandwiched between two nylon nonwoven layers containing 220 mg of silver. This product generally provides very low release of silver and the device itself exhibits an undesirable discoloration.

Other attempts have been made to apply such specific microbicides on the surfaces of fabrics and yarns with little success in terms of controlled release of the microbicide to the wound, prevention of discoloration of the wound care device, and adequate exudate absorption capabilities. To make this device, silver via a solution of silver nitrate is reduced and deposited on sensitized polymeric fibers (typically nylon) via a process referred to as electroless deposition. The silver laden polyamide is attached to a subsequent fiber layer. Because of the nature of this technology, it is difficult to control the amount of silver deposited on the fiber and furthermore, the amount of silver deposited is limited by the surface area of the fiber. Additionally, this product faces challenges with regard to discoloration of the substrate as well. Thus, a topical treatment with silver-based antimicrobial agents has not been successfully developed and applied to a substrate having the combination of characteristics described herein, as desired for an effective wound care device.

A topical treatment for textile substrates, such as a fabric, is desirable because it permits treatment of a fabric's individual fibers before or after weaving, knitting, and the like, in order to provide greater versatility to the target yarn without altering its physical characteristics. It is also advantageous for application to foam materials because antimicrobial agents are not incorporated into the material in areas that will never come into contact with the wound. Such a coating, however, should prove to be successful at releasing a controlled amount of silver to the wound while preventing discoloration of the wound care device to be considered functionally acceptable. Furthermore, it is desirable for such a metallized treatment to be electrically non-conductive on target fabric, fiber, yarn, film and/or foam surfaces. With the presence of metals and metal ions, it has been difficult in the past to obtain such a functional, electrically non-conductive coating for use in wound care devices.

Successful attempts at topically applying a silver-based antimicrobial finish to textile substrates are described in commonly assigned U.S. Pat. No. 6,584,668 and in commonly assigned U.S. patent application Ser. Nos. 09/586,381; 09/586,081; 09/589,179; 09/585,762; 10/307,027, and 10/306,968. All of these patents and patent applications are herein incorporated by reference. The details of many of these processes will be discussed in detail below.

The present invention addresses and overcomes the problems described above. Historically, a microbicide has been incorporated into a melt or polymer matrix prior to the formation of a fiber, foam, or other textile substrate to create an antimicrobial layer useful for wound care devices. The current invention discloses a method for achieving a wound care device having a silver-based antimicrobial finish, which is topically applied to a target substrate. The resultant wound care device provides controlled release of silver to the wound site without discoloring the device and further provides exudate absorption capabilities. The wound care device optionally includes an odor absorbing agent or layer for eliminating or reducing undesirable odors emitted from the wound site. Additional layers may also be included in the composite structure to assist in boosting absorption capacity, such as, for example, one or more layers of foam, alginate, carboxymethyl cellulose, and the like. These additional layers may or may not contain an antimicrobial agent. For these reasons and others that will be described herein, the present wound care device represents a useful advance over the prior art.

BRIEF DESCRIPTION OF THE DRAWINGS

FIG. 1 shows the results of zone of inhibition testing for the control sample and inventive Example 1, when tested against methicillin resistant *Staphylococcus aureus*.

FIG. 2 shows the results of zone of inhibition testing for the control sample, inventive Example 1, and Comparative Examples A - C, when tested against *Staphylococcus aureus*.

FIG. 3 shows the results of zone of inhibition testing for the control sample, inventive Example 1, and Comparative Examples A - C, when tested against *Pseudomonas aeruginosa*.

FIG. 4 illustrates one embodiment of the present invention comprising a multi-layered wound care device.

FIG. 5 shows one variation of the wound care device of FIG. 4 with a removable film layer.

DETAILED DESCRIPTION OF THE INVENTION

Substrate

Suitable substrates for receiving a topically applied silver-based antimicrobial finish include, without limitation, fibers, fabrics, films, foams, alginates, hydrogels, and hydrocolloids. The fabric may be formed from fibers such as synthetic fibers, natural fibers, or combinations thereof. Synthetic fibers include, for example, polyester, acrylic, polyamide, polyolefin, polyaramid, polyurethane, regenerated cellulose, and blends thereof. More specifically, polyester includes, for example, polyethylene terephthalate, polytriphenylene terephthalate, polybutylene terephthalate, polylactic acid, and combinations thereof. Polyamide includes, for example, nylon 6, nylon 6,6, and combinations thereof. Polyolefin includes, for example, polypropylene, polyethylene, and combinations thereof. Polyaramid includes, for example, poly-p-phenyleneteraphthalamid (i.e., Kevlar®), poly-m-phenyleneteraphthalamid (i.e., Nomex®), and combinations thereof. Natural fibers include, for example, wool, cotton, flax, and blends thereof.

The fabric may be formed from fibers or yarns of any size, including microdenier fibers and yarns (fibers or yarns having less than one denier per filament). The fibers or yarns may have deniers that range from less than about 1 denier per filament to about 2000 denier per filament or more preferably, from less than about 1 denier per filament to about 500 denier per filament, or even more preferably, from less than about 1 denier per filament to about 300 denier per filament.

Furthermore, the fabric may be partially or wholly comprised of multi-component or bi-component fibers or yarns which may be splittable along their length by chemical or mechanical action. The fabric may be comprised of fibers such as staple fiber, filament fiber, spun fiber, or combinations thereof.

The fabric may be of any variety, including but not limited to, woven fabric, knitted fabric, nonwoven fabric, or combinations thereof. They may optionally be colored by a variety of dyeing techniques, such as high temperature jet dyeing with disperse dyes, thermosol dyeing, pad dyeing, transfer printing, screen printing, or any other technique that is common in the art for comparable, equivalent, traditional textile products. If yarns or fibers are treated by the process of the current invention, they may be dyed by suitable methods prior to fabric formation, such as, for instance, by package dyeing or solution dyeing, or after fabric formation as described above, or they may be left undyed.

The film may include thermoplastic materials, thermoset materials, or combinations thereof. Thermoplastic or thermoset materials may include polyolefin, polyester, polyamide, polyurethane, acrylic, silicone, melamine compounds, polyvinyl acetate, polyvinyl alcohol, nitrile rubber, ionomers, polyvinyl chloride, polyvinylidene chloride, chloroisoprene, or combinations thereof. The polyolefin may be polyethylene, polypropylene, ethylvinyl acetate, ethylmethyl acetate, or combinations thereof. Polyethylene may include low density or high density polyethylene. The film may have a thickness of between about 1 and about 500 microns, or more preferably between about 1 and about 250 microns, or even more preferable between about 1 and about 100 microns.

Foam generally refers to a cellular polymeric structure, and preferably an open cell structure, Suitable foams include such synthetic organic polymers as polyurethane, carboxylated butadiene styrene rubber, polyester, and polyacrylate. It is generally desirable that the foam is hydrophilic; however, hydrophobic foams having a hydrophilic coating on them may be used.

Alginate is a natural polysaccharide that exists widely in many brown seaweeds. Sodium alginates are well known for their ability to form a gel in contact with most divalent cations. Divalent $Ca^{2+}$ structurally fits into the guluronate blocks, thus binding the alginate polymers together by forming junction zones, resulting in gelation. For example, when in contact with blood, sodium alginate will rapidly exchange for $Ca^{2+}$ ions, thereby making it ideal for wound contact dressings. Fibers may be formed from alginate by extruding or spinning the alginate from an aqueous solution. The fibers are then typically laid down in a web mat which can be incorporated into a wound care device. Alginate may also be incorporated into a foam or other suitable material for enhancing absorbency of the ultimate wound care device.

Hydrogels are stable, moist wound care devices that absorb water through swelling and release water by de-swelling. Hydrogels generally consist of high-molecular molecules that form a coherent matrix for enclosing smaller molecules and aqueous solutions. Hydrogels can be described as a two-component system of water and a three-dimensional network polymer. Examples of hydrogels include starch, pectin, gelatin, and gum.

Hydrocolloids are hydrophilic polymers, of vegetable, animal, microbial or synthetic origin, that generally contain many hydroxyl groups and may be polyelectrolytes. They are naturally present or added to control the functional properties of a material such as viscosity, including thickening and gelling, and water binding. They are advantageous for use as wound care devices because of their ability to absorb several times their weight in wound exudates. Examples of hydrocolloids include carbowax, vinyl polymers (such as polyvinyl alcohol, polyvinyl pyrrolidone, and polyvinylacetate), cellulose derivatives (such as ethyl cellulose, methyl cellulose, and carboxymethyl cellulose), and natural gums (such as guar, acacia, and pectins).

In one embodiment of the invention, a nonwoven fabric is used to form the wound care device. Nonwovens are known in the textile industry as an alternative to traditional woven or knit fabrics. To create a nonwoven fabric, a filament web must be created and then consolidated. In one method, staple fibers are formed into a web through the carding process, which can occur in either wet or dry conditions. Alternatively, continuous filaments, which are formed by extrusion, may be used in the formation of the web. The web is then consolidated, and/or bonded, by means of needle-punching, thermal bonding, chemical bonding, or hydroentangling. A second consolidation method may also be employed such as thermal bonding.

One preferred substrate for use in the wound care device of the present disclosure is a nonwoven fabric formed of continuous splittable filaments that are extruded as a web and then consolidated. This nonwoven fabric is described in U.S. Pat. Nos. 5,899,785 and 5,970,583, both assigned to Freudenberg and incorporated entirely herein by reference. Preferably, the nonwoven web is consolidated through hydroentanglement, and, more preferably, through hydroentanglement followed by thermal, or point, bonding. The continuous composite filaments are obtained by means of a controlled spinning process, and the hydroentanglement process mechanically splits the composite filaments into their elementary components.

The continuous filaments have the following characteristics: (1) the continuous filaments are comprised of at least two elementary filaments and at least two different fiber types; (2) the continuous filaments are splittable along at least a plane of separation between elementary filaments of different fiber types; (3) the continuous filaments have a filament number (that is, titer or yarn count) of between 0.3 dTex and 10 dTex; and (4) the elementary filaments of the continuous filament have a filament number between 0.005 dTex and 2 dTex. Simply put, the nonwoven fabric can be described as a nonwoven fabric of continuous microfilaments. Such a fabric is described in U.S. Pat. Nos. 5,899,785 and 5,970,583, both to Groten et al., each of which is incorporated herein by reference.

As discussed previously, a wide range of synthetic materials may be utilized to create the elementary filaments of the continuous composite filaments. As such, the group of polymer materials forming the elementary filaments may be selected from among the following groups: polyester and polyamide; polyolefin and polyamide; polyester and polyolefin; polyurethane and polyamide; polyester, polyolefin, and polyamide; aliphatic polyester and aromatic polyester; acrylic polymers and polyamides; and other combinations thereof.

The term "polyamide" is intended to describe any long-chain polymer having recurring amide groups (—NH—CO—) as an integral part of the polymer chain. Examples of polyamides include nylon 6; nylon 66; nylon 11; and nylon 610.

The term "polyester" is intended to describe any long-chain polymer having recurring ester groups (—C(O)—

O—). Examples of polyesters include aromatic polyesters, such as polyethylene terephthalate (PET), polybutylene terephthalate (PBT), and polytrimethylene terephthalate (PTT), and aliphatic polyesters, such as polylactic acid (PLA).

The composite filaments can have a variety of configurations. The core portions of the composite filaments can be of one fiber type. Alternatively, fibers having no core portion (that is, hollow core composite filaments) and fibers without a recognizable "core" are suitable for use in the present invention as well. The composite filaments typically have a symmetrical cross-section having a central median axis. However, the composite filament can be unsymmetrical, having elementary filaments with non-uniform cross-sections. The cross-section of the composite filaments can be substantially circular in shape or can be comprised of multiple lobes that are joined at a central region. Another variation of the construction of splittable composite filaments is one having a cross-section in which ribbons, or fingers, of one component are positioned between ribbons, or fingers, of a second different component. Yet another variation includes either one or a plurality of elementary filaments of one material that are Integrated in a surrounding matrix of a second different material.

The nonwoven fabric may have a fabric weight of between about 20 g/m$^2$ and about 300 g/m$^2$, or preferably between about 50 g/m$^2$ and about 200 g/m$^2$, or more preferably between about 80 g/m$^2$ and about 150 g/m$^2$, and most preferably between about 100 g/m$^2$ and about 130 g/m$^2$.

While a potentially preferred nonwoven fabric has been described, it is believed that any microdenier nonwoven fabric that has been treated with the silver-based antimicrobial chemistry described herein would fall within the scope of the present disclosure, as well as any of the above-mentioned substrate materials.

Furthermore, the substrate may be dyed or colored with any type of colorant, such as, for example, pigments, dyes, tints, and the like. Other additives may be present on and/or within the target fabric or yarn, including antistatic agents, brightening compounds, nucleating agents, antioxidants, UV stabilizers, fillers, permanent press finishes, softeners, lubricants, curing accelerators, and the like. The present fabric may also be coated, printed, colored, dyed, and the like.

The particular microdenier nonwoven fabric described above provides many advantages over materials previously used for wound care devices. First, the fabric is surprisingly absorbent, despite its synthetic content, having an absorbency that is substantially equal to that of cotton fabrics. Second, because the fabric is synthetic, the wound care device is very durable and generates less lint than its natural counterpart, representing a reduced likelihood of infection in a wound caused by the lint and fiber from the wound care device itself. Third, the fabric's nonwoven construction does not unravel when cut, thereby further reducing the chance that loose fibers and lint will enter the wound site and lead to possible infection. In addition, the fabric is quite thin and lightweight, as compared with traditional woven cotton fabrics. The thinness of the present fabric facilitates it use as one component of a composite wound care device by not significantly contributing to increased bulk and thickness of the device, thus providing more comfort and ease of use for the patient wearing the device. Finally, the microdenier structure of the present fabric provides a greater surface area onto which the antimicrobial agent may be applied, thus effectively increasing the amount of surface-available silver. These advantages represent a useful advancement over the prior art.

Antimicrobial and Other Agents

The particular treatment used herein comprises at least one type of silver-ion containing compounds, or mixtures thereof of different types. The term "silver-ion containing compounds" encompasses compounds that are either ion-exchange resins, zeolites, or, possibly, substituted glass compounds that release the particular metal ion bonded thereto upon the presence of other anionic species. The preferred silver-ion containing compound for this invention is an antimicrobial silver sodium hydrogen zirconium phosphate available from Milliken & Company, under the tradename AlphaSan®. Other potentially preferred silver-containing antimicrobials in this invention, including silver zeolites, such as those available from Sinanen under the tradename Zeomic® AJ, silver exchanged on calcium phosphate available from Sangi under the tradename of Apiscider, and silver glass, such as those available from Ishizuka Glass under the tradename Ionopure®, may be utilized either in addition to, or as a substitute for, the preferred species. Other silver ion containing materials may also be used. Various combinations of these silver containing materials may be made if it is desired to "tune" the silver release rate over time.

Generally, such a metal compound is added in an amount from about 0.01% to about 60% by total weight of the particular treatment composition; more preferably, from about 0.05% to about 40%; and most preferably, from about 0.1% to about 30%. Preferably, the metal compound is present in an amount from about 0.01% to about 60% of the weight of the fabric (owf), preferably from about 0.05% to about 30% owf, more preferably from about 0.1% to about 10% owf, and most preferably from about 0.3% to about 3.0% owf. The treatment itself, including any necessary binders, wetting agents, odor absorbing agents, leveling agents, adherents, thickeners, and the like, is added to the substrate in an amount of at least about 0.01%.

The binder material provides highly beneficial durability of the antimicrobial compound for the target substrate. Preferably, this component is a polyurethane-based binding agent, although other binders, such as a permanent press type resin or an acrylic type resin, may also be used in combination, particularly with the halide ion additive for discoloration reduction. In essence, such resins provide durability by adhering silver to the target substrate, such as fibers or fabrics, with the polyurethane exhibiting the best overall performance.

The odor receiving agent can be a odor absorbing agent, and/or an odor adsorbing agent. Odor absorbing agents receive the odor and trap that odor inside the agent. Odor adsorbing agents receive the odor and hold the odor on the exterior of the agent. The odor receiving agent can be a particulate odor receiving agents, such as activated carbon, charcoal, zeolite compounds, or the like. Particulate odor receiving agents provide a greater surface area for receiving the odorous material. A carbonaceous material that can be converted into an activated carbon for the present invention include materials such as coal (bituminous), coconut shells, coke, peat, petroleum fractions, wood chips (saw dust), or the like. Other less common materials that can be used for forming activated carbon include automobile tires, cherry stones, coffee grounds, corn cobs, plastic waste, sewage sludge, straw, water lilies, or the like. Performance of the activated charcoal is typically improved with greater pore size and surface area. Generally, the smaller the particulate size, the better the odor receiving capability of the odor receiving agent.

Total add-on levels of silver to the target substrate may be 20 ppm or higher. More preferably, total add-on levels of silver may be 200 ppm or higher. It has not been determined that an upper boundary limit of silver add-on levels to the target substrate exist. However, consideration should be taken of the wound site itself and prevention of any irritation to the site or to the patient from excessive silver should be avoided.

Application Method

The preferred procedure utilizes silver-ion containing compounds, such as either AlphaSan®, Zeomic®, or Ionpure® as preferred compounds (although any similar types of compounds that provide silver ions may also be utilized), which are admixed with a binder to form a bath, into which the target substrate is then immersed.

It was initially determined that proper binder resins could be selected from the group consisting of nonionic permanent press binders (i.e., cross-linked adhesion promotion compounds, including, without limitation, cross-linked imidazolidinones available from Sequa under the tradename Permafresh®) or slightly anionic binders (including, without limitation, acrylics such as Rhoplex® TR3082 from Rohm & Haas). Other nonionics and slightly anionics were also suitable, including melamine formaldehyde, melamine urea, ethoxylated polyesters (such as Lubril QCX™, available from Rhodia), and the like. However, it was found that the durability and controlled silver release of such treated substrates was limited.

It was determined that greater durability and control over silver release was required for this type of wound care application. Thus, these prior comparative treatments were measured against various other types. Finally, it was discovered that certain polyurethane binders (such as Witcobond® from Crompton Corporation) and acrylic binders (such as Hystretch® from BF Goodrich) permitted the best overall durability and controlled release of silver ion.

With such specific polyurethane-based binder materials utilized, the antimicrobial characteristics of the treated substrate remained very effective with regard to the amount of surface available silver that could be controllably released to kill bacteria, without discoloration of the treated substrate. However, while it currently appears that the use of polyurethane based binder resins are preferred due to their silver release and bio-neutral properties, in practice essentially any binder resin which is not toxic to the wound may be used.

An acceptable method of providing a durable antimicrobial metal-treated fabric surface, is the application of a silver-ion containing compound and polyurethane-based binder resin from a bath mixture. In practice, this mixture of compound and resin may be applied through spraying, dipping, padding, foaming, and the like.

As mentioned previously, it has been recognized that silver-ion topical treatments are susceptible to yellowing, browning, graying, and, possibly, blacking after exposure to atmospheric conditions. As silver ions are generally highly reactive with free anions, and most anions that react with silver ions produce color, a manner of curtailing, if not outright preventing, problematic color generation upon silver ion interactions with free anionic species, particularly within dye bath liquids, was required. Thus, it was theorized that inclusion of an additive that was non-discoloring itself, would not react deleteriously with the binder and/or silver-ion compound, and would apparently, and without being bound to any specific scientific theory, react in such a manner as to provide a colorless salt with silver ions, was highly desired.

Several methods for achieving this result are described in commonly assigned U.S. patent application Ser. Nos. 10/307,027; 10/306,968; and 10/418,019, all of which are entirely incorporated by reference herein. These Applications describe methods of including halide ions, such as from metal halides like magnesium chloride, in the silver-ion topical treatment to react with silver ions to produce colorless salts. The inclusion of halide ions, such as from metal halides (for example, magnesium chloride) or hydrohalic acids (for example, hydrogen chloride) provide such results, with the exception that the presence of sodium ions (which are of the same valence as silver ions, and compete with silver ions for reaction with halide ions) should be avoided, since such components prevent the production of colorless silver halides, leaving the free silver ions the ability to react thereafter with undesirable anions. Thus, the presence of monovalent sodium ions (as well as other monovalent alkali metal ions, such as potassium, cesium, and lithium, at times) does not provide the requisite level of discoloration reduction. In general, amounts of 20 ppm or greater of sodium ions within the finish composition, particularly within the solvent (water, for example) are deleterious to the discoloration prevention of the topically applied antimicrobial treatments. Thus the term "substantially free from sodium ions" is used to indicate a presence of no more than this threshold amount of 20 ppm, and, more preferably, no more than 5 ppm.

Furthermore, the divalent or trivalent (and some monovalent) metal halide counteracts some effects of sodium ion exposure if present in a sufficient amount within the finish composition. Thus, higher amounts of sodium or like alkali metal ions are present within the finish composition; higher amounts of metal halide, such as magnesium chloride, for example, can counterbalance the composition to the extent that discoloration can be properly prevented. Additionally, all other metal ions—whether divalents, trivalents, and the like, with divalents, such as magnesium, being most preferred—combined with halide anions (such as chlorides, bromides, iodides, as examples, with chloride most preferred), as well as acids (such as HCl, HBr, and the like), are potential additives for discoloration prevention.

The concentrations of chloride ion should be measured in terms of molar ratios with the free silver ions available within the silver-ion containing compound. A range of ratios of chloride to silver ions should be from 1:10 to 5:1 for proper discoloration prevention; preferably, the range is from 1:2 to about 2.5:1. Again, higher amounts of metal halide in molar ratio to the silver ions may be added to counteract any excess alkali metal ion amounts within the finish composition itself.

Since the color control technique mentioned above retards the free release of silver ions from the system, it is not surprising that measurements made using the "silver elution test" discussed further below show a decrease in available silver as the concentration ratio of chloride to silver ions is increased. A nonobvious result to one skilled in this art is that the "zone of inhibition" testing did not show a deleterious effect due to the reduction in silver release (i.e. the zones were not smaller in size when the chloride to silver ion ratio was increased by 10×). Even more surprising was the result observed in the repeat exposure zone of inhibition testing which indicate that the longevity of the silver release in the wound care device is actually improved as the chloride to silver ion ratio was increased.

The following examples further illustrate the present antimicrobial article but are not to be construed as limiting the invention as defined in the claims appended hereto. All parts and percents given in these examples are by weight unless otherwise indicated.

The fabric used in Examples 1 and 2 was a point-bonded nonwoven fabric, available under the tradename Evolon® from Firma Carl Freudenberg of Weinheim, Germany, having a fabric weight of 130 g/m². The fabric was comprised of spun-bonded continuous multi-component fibers which have been exposed to mechanical or chemical processes to cause the multi-component fibers to split, at least partially, along their length into individual polyester and nylon 6,6 fibers, according to processes described in the two Freudenberg patents earlier incorporated by reference. The polyester fiber comprised about 65% of the fabric, and the nylon 6,6 fiber comprised about 35% of the fabric. The fabric was not dyed.

The fiber used in Example 3 was a 70 denier 34 filament Dacron® polyester fiber.

The foam used in Example 4 was standard, non-antimicrobially foam used in the wound care industry today.

Various solutions of an antimicrobial finish containing AlphaSan® silver-based ion exchange compound (available from Milliken & Company of Spartanburg, S.C. were produced for topical application via bath to the target substrate. The formulations (excluding water) based on 100 parts of antimicrobial agent are as follows:

EXAMPLE 1

Evolon® Nonwoven Fabric

| Component | Amount (parts) |
| --- | --- |
| Witcobond 293 (polyurethane binder) | 75 |
| AlphaSan ® RC 2000 (antimicrobial agent, 10% Ag) | 100 |
| Lubril QCJ (ethoxylated polyester, wetting agent) | 39 |
| Freecat MX (magnesium chloride, color stabilizing agent) | 2 |

EXAMPLE 2

Evolon® Nonwoven Fabric

| Component | Amount (parts) |
| --- | --- |
| Witcobond 293 (polyurethane binder) | 74 |
| AlphaSan ® RC 2000 (antimicrobial agent) | 100 |
| Lubril QCJ (ethoxylated polyester, wetting agent) | 39 |
| Freecat MX (magnesium chloride, color stabilizing agent) | 20 |

EXAMPLE 3

Evolon® Nonwoven Fabric

| Component | Amount (in grams) |
| --- | --- |
| Water | 961.1028 |
| Witcobond 293 (polyurethane binder) | 331.6750 |
| AlphaSan ® RC 2000 (antimicrobial agent) | 444.4444 |
| Lubril QCJ (ethoxylated polyester, wetting agent) | 173.8888 |
| Freecat MX (magnesium chloride, color stabilizing agent) | 88.8888 |

EXAMPLE 4

Evolon® Nonwoven Fabric

| Component | Amount (in grams) |
| --- | --- |
| Water | 1740.2758 |
| Witcobond 290H (polyurethane binder) | 82.9188 |
| AlphaSan ® RC 2000 (antimicrobial agent) | 111.1112 |
| Lubril QCJ (ethoxylated polyester, wetting agent) | 43.4722 |
| Freecat MX (magnesium chloride, color stabilizing agent) | 22.2222 |

EXAMPLE 5

Evolon® Nonwoven Fabric

| Component | Amount (in grams) |
| --- | --- |
| Water | 961.1028 |
| Witcobond 290H (polyurethane binder) | 331.6750 |
| AlphaSan ® RC 2000 (antimicrobial agent) | 444.4444 |
| Lubril QCJ (ethoxylated polyester, wetting agent) | 173.8888 |
| Freecat MX (magnesium chloride, color stabilizing agent) | 88.8888 |

EXAMPLE 6

Foam

| Component | Amount (parts) |
| --- | --- |
| Witcobond 293 (polyurethane binder) | 75 |
| AlphaSan ® RC 2000 (antimicrobial agent) | 100 |
| Lubril QCJ (ethoxylated polyester, wetting agent) | 39 |
| Freecat MX (magnesium chloride, color stabilizing agent) | 2 |

EXAMPLE 7

Polyester Fiber

| Component | Amount (parts) |
| --- | --- |
| Witcobond 293 (polyurethane binder) | 100 |
| AlphaSan ® RC 2000 (antimicrobial agent) | 100 |

For Examples 1 through 5, the solution was formulated into water and applied to the nonwoven fabric via pad and nip rolls. Examples 1 through 5 yield an antimicrobial agent content of 1.7%, 2.2%, 18.1%, 5.1%, 18.4% owf, respectively. A control fabric of untreated Evolon® nonwoven fabric was also prepared in a water-only solution, which was exposed to the same process conditions as Examples 1 through 5 to be used as a comparison control.

For Example 6, the solution was formulated with water and applied via spray to achieve approximately 4.2% antimicrobial agent content based on weight of the foam.

For Example 7, the solution described was formulated with water and applied to 70/34 polyester fiber using an Atlab finish applicator manufactured by Atlas Industries to achieve approximately 7.5% antimicrobial agent content on the fiber. Prior to testing for zone of inhibition described below, 12 strands of this fiber were hand twisted into a yarn ca. 5 cm in length.

Each of the above examples was tested for a variety of characteristics as described below. In addition, several currently available silver-containing wound care devices were also tested. They are notated as Comparative Examples A-E below and include a wide variety of wound dressing combinations such as multi-layered fabrics, foams, and hydrocolloids.

COMPARATIVE EXAMPLE A

Actisorb 220, a multi-component nonwoven wound care device comprised of a highly porous, silver impregnated charcoal cloth sandwiched between two nylon nonwoven layers containing 220 mg of silver; available from Johnson & Johnson

COMPARATIVE EXAMPLE B

Acticoat 5, a three layered wound care device having a rayon/polyester blend layer of nonwoven fabric sandwiched between two layers of nanocrystalline silver coated polyethylene film; available from Smith and Nephew

COMPARATIVE EXAMPLE C

Acticoat 7, a five layered wound care device similar to Acticoat B that has additional layers of fabric and film; also available from Smith and Nephew

COMPARATIVE EXAMPLE D

Contreet F, a polyurethane foam having 13% AlphaSan® RC 2000 silver throughout the polymer matrix; available from Coloplast A/S

COMPARATIVE EXAMPLE E

Contreet H, a hydrocolloid having silver sodium thiosulfate throughout the polymer; also available from Coloplast A/S Zone of Inhibition Test Examples 1 through 7 and the Comparative Examples were tested against one or more of *Staphylococcus aureus* ATCC #6538, *Pseudomonas aeruginosa* ATCC #12055, and Methicillin-Resistant *Staphylococcus aureus* ATCC #43300 using a standard zone of inhibition test based on the Kirby-Bauer Agar-Diffusion Assay. The agar plates were incubated for 24 hours at 37 degrees C. Examples 3 and 4 were tested against *Staphylococcus aureus* ATCC #6538 and *Klebsiella pneumoniae* ATCC #4352 using the same standard zone of inhibition test. The zone of inhibition assay ("ZOI Assay") provides both a qualitative (level of growth underneath sample) and quantitative (size of zone in mm) assessment of the performance of an antimicrobial agent incorporated into a wound dressing. The level of growth underneath the sample can be rated from confluent (no activity), to spotty or isolated (bacteriostatic), to nil (bactericidal). If reduced growth is observed underneath the sample for a particular microorganism compared to an untreated control dressing, that microorganism is considered sensitive and the antimicrobial agent is effective (bacteriostatic). The magnitude of the zone of inhibition, If one is observed, is a measure of both the inherent efficacy of the agent and the diffusion of the agent through the nutrient agar matrix. This zone of Inhibition assay can be used to measure the efficacy of the dressings in a simulated clinical application by subjecting the dressings to multiple insults of a high level of bacteria over a period of seven days. The Control sample was generally a Medisponge® polyurethane foam available from Lendell, an antimicrobial-free substrate.

The results shown In Tables 1A - 1D below, represented by an average of 4 measurements from 4 sides of the square sample, and in FIGS. 1 - 3, demonstrate that Inventive Examples 1 through 7 which contained AlphaSan® RC 2000 were antimicrobially active against the various types of bacteria. In comparison, the control sample, which did not contain any antimicrobial agent, did not demonstrate antimicrobial activity against any of the bacteria. Furthermore, while the Comparative Examples exhibited antimicrobial activity, in most instances, the zone of inhibition was larger for the inventive Examples 1 through 7. This indicated that inventive Examples 1 through 7, in most instances, demonstrated greater antimicrobial activity than the Comparative Examples.

The results shown in Tables 1A-1D below, represented by an average of 4 measurements from 4 sides of the square sample, and in FIGS. 1-3, demonstrate that inventive Examples 1 through 11 which contained AlphaSan® RC 2000 were antimicrobially active against the various types of bacteria. In comparison, the control sample, which did not contain any antimicrobial agent, did not demonstrate antimicrobial activity against any of the bacteria. Furthermore, while the Comparative Examples exhibited antimicrobial activity, in most instances, the zone of inhibition was larger for the inventive Examples 1 through 11. This indicated that inventive Examples 1 through 11, in most instances, demonstrated greater antimicrobial activity than the Comparative Examples.

Additionally, FIGS. 2 and 3 demonstrate the effectiveness of the topically applied antimicrobial finish in preventing discoloration of the target substrate. Example 1 has maintained its original white appearance, while all of the Comparative Examples are darker in color due to the presence of silver and/or carbon particles contained within the wound care devices. Furthermore, while FIG. 1 shows Example 1 has a darkened appearance, this effect was deliberately created using dye to enhance the contrast of Example 1 against the background color of the plate and the zone of inhibition for photography purposes. Example 1 did not discolor due to the topical application of the antimicrobial finish.

TABLE 1A

Antimicrobial Activity Against *Staphylococcus aureus* As Determined By Zone of Inhibition Method

| Sample | Average Day 1 Zone (mm) | Day 1 Swab Results | Day 1 Swab Conclusion | Average Day 2 Zone (mm) | Average Day 3 Zone (mm) | Average Day 4 Zone (mm) |
|---|---|---|---|---|---|---|
| Example 1 | 5.3 | No Growth | Bactericidal | 0.5 | 0 | n/a |
| Example 2 | 4.4 | No Growth | Bactericidal | 3.0 | 3.0 | 3.0 |
| Example 3 | 4.0 | No Growth | Bactericidal | 3.0 | 2.8 | 3.0 |
| Example 4 | 4.4 | No Growth | Bactericidal | 2.0 | 0.8 | 2.5 |
| Example 5 | 1.0 | No Growth | Bactericidal | 0.5 | 0 | 0 |
| Example 7 | 3.0 | No Growth | Bactericidal | n/a | n/a | n/a |
| Comparative Example A | 0.8 | Few Isolated Colonies | Bacteriostatic | n/a | n/a | n/a |
| Comparative Example B | 3.5 | No Growth | Bactericidal | n/a | n/a | n/a |
| Comparative Example C | 4.3 | No Growth | Bactericidal | n/a | n/a | n/a |
| Comparative Example D | 2.0 | No Growth | Bactericidal | n/a | n/a | n/a |
| Control | 0 | Confluent Growth | No Effect | 0 | 0 | 0 |

TABLE 1B

Antimicrobial Activity Against *Pseudomonas aeruginosa* As Determined By Zone of Inhibition Method

| Sample | Average Day 1 Zone (mm) | Day 1 Swab Results | Day 1 Swab Conclusion | Average Day 2 Zone (mm) | Average Day 3 Zone (mm) | Average Day 4 Zone (mm) |
|---|---|---|---|---|---|---|
| Example 1 | 5.9 | No Growth | Bactericidal | 2.1 | 0.5 | n/a |
| Example 2 | 7.8 | No Growth | Bactericidal | 6.0 | 5.5 | 4.5 |
| Example 3 | 6.3 | No Growth | Bactericidal | 6.8 | 6.0 | 4.0 |
| Example 4 | 6.8 | No Growth | Bactericidal | 4.8 | 2.8 | 2.5 |
| Example 5 | 6.0 | No Growth | Bactericidal | 0.8 | 0.5 | 0 |
| Comparative Example A | 0.5 | No Growth | Bactericidal | n/a | n/a | n/a |
| Comparative Example B | 6 | No Growth | Bactericidal | n/a | n/a | n/a |
| Comparative Example C | 6.5 | No Growth | Bactericidal | n/a | n/a | n/a |
| Control | 0 | Confluent Growth | No Effect | 0 | 0 | 0 |

TABLE 1C

Antimicrobial Activity Against Methicillin-Resistant *Staphylococcus aureus* As Determined By Zone of Inhibition Method

| Sample | Average Day 1 Zone (mm) | Day 1 Swab Results | Day 1 Swab Conclusion |
|---|---|---|---|
| Example 1 | 3.00 | No Growth | Bactericidal |
| Comparative Example B | 3.00 | No Growth | Bactericidal |
| Control | 0 | Confluent Growth | No Effect |

TABLE 1D

Antimicrobial Activity Against *Klebsiella pneumoniae* As Determined By Zone of Inhibition Method

| Sample | Average Day 1 Zone (mm) | Day 1 Swab Results | Day 1 Swab Conclusion |
|---|---|---|---|
| Example 7 | 3.00 | No Growth | Bactericidal |
| Comparative Example B | 3.00 | No Growth | Bactericidal |
| Comparative Example C | 3.00 | No Growth | Bactericidal |
| Comparative Example D | 3.00 | No Growth | Bactericidal |
| Control | 0.00 | Confluent Growth | No Effect |

Silver Elution Test

The samples were tested to determine their ability to controllably release surface available silver. Each sample was immersed in a container holding 100mM of an aqueous sodium potassium phosphate extraction solution, which is used to simulate serum or wound exudate fluid. The sample was shaken at room temperature for 24 hours. The extract was then analyzed by inductively coupled plasma measurements for a measurement of available silver removed from the surface of the sample. The Control sample was an untreated piece of Evolon® nonwoven fabric.

The results are shown in Table 2 below. The results indicate that inventive Examples 1 and 2 provide a controlled release of surface available silver, which is advantageous for a wound care device. The results also demonstrate that Comparative Example A released very little silver, which indicates that the wound care device may not provide adequate antimicrobial properties to the wound site. Additionally, Comparative Examples B and C dumped a lot of silver over a 24 hour period, which may lead to irritation of the wound site due to the excessive amount of silver released so quickly.

The results are shown in Table 2 below. The results indicate that inventive Examples 1 through 5 provide a controlled release of surface available silver, which is advantageous for a wound care device. The results also demonstrate that Comparative Example A released very little silver, which indicates that the wound care device may not provide adequate antimicrobial properties to the wound site. Additionally, Comparative Examples B and C dumped a lot of silver over a 24 hour period, which may lead to irritation of the wound site due to the excessive amount of silver released so quickly.

Thus, the results illustrate that the topically applied antimicrobial finish of Examples 1 and 2 achieve the most desirable release rate of silver and zone of inhibition without overdosing the silver into the wound. Accordingly, it may be desirable that the wound care device release less than about 50 µg/cm² of silver over a 24 hour period. It may be more preferable that the wound care device release less than about 25 µg/cm² of silver over a 24 hour period. Furthermore, it may be most preferable that the wound care device release less than about 10 µg/cm² of silver over a 24 hour period.

TABLE 2

Silver Elution of Antimicrobial Wound Care Devices

| Sample ID | Silver Elution (µg/cm2) |
|---|---|
| Example 1 | 5.3 |
| Example 2 | 1.1 |
| Comparative Example A | 0.2 |
| Comparative Example B | 33.0 |
| Comparative Example C | 35.1 |
| Control | 0.0 |

Total ALPHASAN® Content Test

The amount of active ALPHASAN® compound transferred to the fabric of Examples 1 through 5 in the application process was determined using the following Ash Procedure technique.

In the Ash Procedure technique, a sample of fabric (weighing approximately 10 grams and measured to four significant digits) was placed in a clean, dry crucible. The crucible containing the fabric sample was placed in a muffle furnace whose temperature ramped up at 3° C./minute to 750° C. The temperature was then held at 750° C. for one hour. The system was then cooled and the crucible transferred to a desiccator in which it was allowed to reach an equilibrium temperature. The crucible was then weighed.

In the Ash Digestion technique, the fabric sample was then ground in the crucible to obtain a uniform sample of approximately 0.1 g weight (again measured to four significant digits). Four milliliters of 50% $HNO_3$, followed by 10 drops of 48% HF, were added to the sample. The sample was heated over a hot plate in a platinum crucible until it completely dissolved. The sample solution was then transferred to a 100 mL volumetric flask.

The crucible was then rinsed with 5% $HNO_3$, with the rinse solution being added to the flask. The solution was diluted to the 100 mL mark with 5% $HNO_3$. The dilute solution was transferred to a polyethylene storage container. Analysis for the desired active ingredient (in this case, silver) was performed using an Inductively Coupled Plasma device (e.g., a Perkin Elmer Optima 4300DV). Calculations are apparent to one skilled in the art. For Examples 1 through 5, the level of the active ALPHASAN® compounds on the inventive fabrics was determined to be approximately 1.7%, 2.2%, 18.1%, 5.1%, and 18.4% on weight of fabric, respectively.

Biological Testing

Examples 1 and 2 and the Comparative Examples were tested for antimicrobial performance. Efficacy against bacteria was assessed using a modified version of AATCC Method 100-1999. Portions (approximately 0.5 g) of each fabric or fiber sample were placed in glass vials and exposed to two types of bacteria—*Staphylococcus aureus* ATCC #6538 (0.5 ml of 1.31 E+06 cells/mL) and *Pseudomonas aeruginosa* ATCC #12055 (0.5 ml of 2.63E+05 cells/ml)—each of which was suspended in 100 mM sodium postassium phosphate buffer for 18-22 hours at 37° C. After incubation, the samples were washed to remove attached cells. The number of viable cells in the wash solution was quantified using a microtiter plate-based "Most Probable Number" assay. The "Control" is a piece of untreated Evolon® nonwoven fabric. The "Maximum Log Reduction Kill Value" is based on the logarithm of the number of bacteria added to the sample minus the logarithm of the minimum number of bacteria that can be counted in the test.

The results are shown in Table 3 below. Negative values, as shown for the Control, indicate bacterial growth. The results demonstrated that inventive Examples 1 and 2 provided effective antimicrobial treatment against both types of bacteria. Furthermore, Example 2, like the Comparative Examples, was capable of achieving maximum log reduction for *Pseudomonas aeruginosa*.

TABLE 3

Efficacy of Antimicrobial Wound Care Devices
As Determined By Log Reduction Kill Values

| Sample ID | S. aureus | P. aeruginosa |
|---|---|---|
| Example 1 | 2.3 | 3.8 |
| Example 2 | 2.4 | 4.2 |
| Comparative Example A | 4.5 | 3.8 |
| Comparative Example B | 4.5 | 3.8 |
| Comparative Example C | 4.5 | 3.8 |
| Comparative Example E | 2.8 | n/a |
| Control | −0.2 | −2.5 |

Exudate/Moisture Absorption Test

In order to determine the amount of exudate or moisture the samples may absorb, the absorption capacity of each sample was calculated. A piece of each sample having a bulk surface area of 39.27 cm$^2$, was place into a container with a solution of 100 mL of a Na$^+$/Ca$^{2+}$Cl$_{n(aq)}$ which contained 142 mmol/L of Na$^+$ and 2.5 mmol/L of Ca$^{2+}$. This specific solution was provided to simulate serum or wound exudate fluid. After 24 hours, the samples were allowed to drip for 1 minute, and then they were reweighed. The absorption capacity (g/cm$^2$/24 h) was calculated from the difference in weight of each sample before and after the 24 hour absorption period.

The results in Table 4 indicate that the inventive, non-woven, single layer wound care devices of Examples 1 and 2, were capable of absorbing between about 20% to about 40% as much liquid as the multi-layered Comparative Examples. The results also show that the topically applied antimicrobial finish does not cause a significant reduction in the inherent absorption characteristics of the uncoated, or Control, sample. Thus, the topically applied antimicrobial finish of the present invention provides the much desired exudate absorption characteristics to these novel wound care devices, when compared with other multi-layered devices.

TABLE 4

Absorption Capacity of Antimicrobial Wound Care Devices

| Sample ID | Absorption Capacity (g/100 cm$^2$/24 hours) |
|---|---|
| Example 1 | 1.64 |
| Example 2 | 1.51 |
| Comparative Example A | 4.75 |
| Comparative Example B | 4.41 |
| Comparative Example C | 7.60 |
| Control | 1.72 |

Moisture Vapor Transmission Rate Test

Moisture vapor transmission rates (MVTR) were calculated for each sample according to test method ASTM E96. MVTR may be used to extrapolate the breathability of the wound care device, or its ability to regulate the water vapor loss from the wound area beneath the wound dressing. Generally, the higher the MVTR, the better the breathability of the wound care device. Each sample was placed over a mason jar and secured with the ring portion of the mason jar lid. The mason jar, containing 330 ml of water, was weighed prior to a 24-hour test period and was then re-weighed after the 24-hour test period. The difference in weight of the jar, in combination with the size of fabric that covered the opening of the jar, determined how much water was transmitted through the fabric over the 24-hour test period.

The results are shown in Table 5 below. The results demonstrate that the topical application of the antimicrobial finish does not significantly reduce the moisture vapor transmission rate of the inventive wound care devices. Furthermore, in some instances, the results illustrate that inventive Examples 1 and 2 are capable of achieving higher MVTRs than the Comparative Examples, which is desirable for regulating moisture loss from the wound site. Accordingly, an MVTR of at least 500 g/m$^2$/24 hours may be preferable. However, an MVTR of at least 550 g/m$^2$/24 hours may be more preferable, and an MVTR of at least 600 g/m$^2$/24 hours may be most preferable.

TABLE 5

Moisture Vapor Transmission Rate
of Antimicrobial Wound Care Devices

| Sample ID | Moisture Vapor Transmission Rate (g/m$^2$/24 hours) |
|---|---|
| Example 1 | 601 |
| Example 2 | 567 |
| Comparative Example A | 551 |
| Comparative Example B | 590 |
| Comparative Example C | 562 |
| Control | 618 |

EXAMPLES 8A-E

Further investigation was done using the same Evolon® nonwoven fabric of Examples 1 through 5 to determine the effects of varying levels of silver, binder, and other components on silver elution and antimicrobial efficacy. Several 500 gram mixes were prepared having different amounts of binder, silver, wetting agent, and color stabilizer.

Five 500-gram mixes of antimicrobial finish containing AlphaSan® silver-based ion exchange compound were produced for topical application via bath to the target fabric. The formulations are shown below with the component amounts measured in grams:

| Component | Example 8A | Example 8B | Example 8C | Example 8D | Example 8E |
|---|---|---|---|---|---|
| Water | 473.7269 | 237.2689 | 355.3877 | 414.4471 | 443.9768 |
| Witcobond 293 | 15.5069 | 155.0688 | 77.5344 | 38.7672 | 19.3836 |
| AlphaSan ® RC 2000 | 2.5974 | 25.9740 | 25.9740 | 25.9740 | 25.9740 |
| Lubril QCJ | 8.1169 | 81.1688 | 40.5844 | 20.2922 | 10.1461 |
| Freecat MX | 0.0519 | 0.5195 | 0.5195 | 0.5195 | 0.5195 |

Each solution was then applied to the sample fabric via pad and nip rolls. A control sample was also prepared in a water-only solution, which was exposed to the same process conditions as Examples 8A-8E.

The samples were tested for silver release and antimicrobial efficacy. Silver release was determined using a silver elution test different from the silver elution test described previously. For Examples 8A-8E, silver elution was performed by immersing each sample in a static solution of $Na^+/Ca^{2+}Cl_n^-$ (aq), which is used to simulate serum or wound exudate fluid, and allowing it to rest for 22 hours at 37 degrees C. The extract was then analyzed by inductively coupled plasma measurements for a measurement of available silver removed from the surface of the sample. The antimicrobial efficacy of the samples was determined using zone of inhibition testing, as previously described. The results of the tests are shown in Tables 6 and 7 below.

The results demonstrate that by varying the amount of a specific component in a given formula, one is capable of tailoring the silver release and antimicrobial properties of the wound care device. Specifically, as the amount of binder is decreased from 20% to 2.5%, the zone of inhibition increased for *Staphylococcus aureus*, which generally indicates that those Examples with larger zones are more effective at killing the bacteria. Additionally, while the amount of silver released during the silver elution testing, it was generally observed that no immediate dumping of excessive amounts of silver occurred during the 22 hour elution. This implies that the amount of components added to all of the formulas may achieve a desirable range for optimum performance of the wound care device.

Another feature discovered with regard to Examples 8A - 8E was that as the amount of binder decreased, the samples exhibited less discoloration. Example 8B, for instance, which contained 20% Witcobond 293, showed some pinkish and light tan discoloration. In contrast, Examples 8A and 8E displayed no discoloration at all. Accordingly, in order to achieve a wound care product that exhibits no or very little discoloration, it may be very important to consider the proportion of one component to another that is added to create the final formulation for a given wound care device.

TABLE 6

Antimicrobial Activity Against *Staphylococcus aureus* As Determined By Zone of Inhibition Method

| Sample | Average Day 1 Zone (mm) | Day 1 Swab Results | Day 1 Swab Conclusion |
|---|---|---|---|
| Example 8A | 2.0 | No Growth | Bactericidal |
| Example 8B | 3.0 | No Growth | Bactericidal |
| Example 8C | 3.3 | No Growth | Bactericidal |
| Example 8D | 3.5 | No Growth | Bactericidal |
| Example 8E | 4.0 | No Growth | Bactericidal |
| Control | 0.00 | Confluent Growth | No Effect |

TABLE 7

Silver Elution of Antimicrobial Wound Care Devices

| Sample ID | Silver Elution (ppm) |
|---|---|
| Example 8A | 1.139 |
| Example 8B | 0.774 |
| Example 8C | 1.246 |
| Example 8D | 2.187 |
| Example 8E | 1.538 |
| Control | 0.010 |

As described previously, any of the substrates described herein may be used alone as a wound care device, including fabrics, films, foams, alginates, hydrogels, and hydrocolloids. Alternatively, one or more of these substrates may be joined together in any possible combination to form a composite, multi-layered, wound care device. The layers may be joined together through various techniques such as ultrasonic welding, heat or pressure lamination, the use of adhesives, needle punching, hydraulic needling, sewing, or other fiber and/or fabric layer laminating or joining processes known to those skilled in the art. The layers may be joined together only at intermittent locations or the layers may be joined together completely.

The topical antimicrobial finish of the current invention may be applied to any one or more of the substrate layers comprising the composite wound care device. Additionally, an odor absorbing agent or layer may be included on or within one or more layers of the composite wound care device. Furthermore, in some instances, the wound care device may have an adhesive layer so that the device may be held in place over the wound site. In such cases, a layer of removable film may be placed over the wound-facing side of the wound care device to protect the adhesive layer until ready for use. Alternatively, the wound care device may be held in place by wrapping long pieces of wound dressing, such as gauze, over and around the wound care device and securing the free end in place by any suitable means, such as pins, clips, or hooks.

One such composite wound care device is shown in FIG. 4 and FIG. 5. FIG. 4 depicts a three layer wound care device 1 in relation to a wound 2 wherein a wound-facing layer 3 has a topically applied antimicrobial finish on its surfaces and, optionally, a layer of adhesive 4 on the outer perimeter of the wound-facing layer 3. Attached to layer 3 is a second layer 5 which optionally contains an odor absorbing agent or layer and optionally also has a topically applied antimicrobial finish on its surfaces. Attached to layer 5 is an outer layer 6 which, similar to layer 5, may optionally contain an odor absorbing agent or layer and optionally also has a topically applied antimicrobial finish on its surfaces. FIG. 5 depicts the wound care device 1 of FIG. 4, except that it also illustrates that a removable film 7 may be applied to the wound-facing layer 3 to protect the adhesive 4. Each of wound-facing layer 3, second layer 5, and outer layer 6 may be comprised of any of the previously described substrates used for forming wound care devices, including fabrics, foams, films, alginates, hydrogels, and hydrocolloids.

Thus, the above description and examples show that a topical antimicrobial finish may be applied to a variety of substrates to achieve an antimicrobially effective, silver-containing wound care device having the desired characteristics of antimicrobial efficacy, controlled release of silver, odor absorption, exudate absorption, and lack of discoloration.

These and other modifications and variations to the present invention may be practiced by those of ordinary skill in the art, without departing from the spirit and scope of the present invention. Furthermore, those of ordinary skill in the art will appreciate that the foregoing description is by way of example only, and is not intended to limit the scope of the invention described in the appended claims.

We claim:

1. A substrate having a surface, at least a portion of which is coated with a non-electrically conductive finish, wherein said finish consists essentially of:
   (a) 0.01 to 60 weight percent of at least one compound delivering silver ions, and
   (b) an aqueous polyurethane binder system;
wherein the ratio of said at least one compound delivering silver ions to said binder system is in the range of 1:1 to 1.35:1 and wherein the coated substrate is an absorbent fabric.

2. The substrate of claim 1, wherein said at least one compound delivering silver ions is a silver ion exchange material.

3. The substrate of claim 2, wherein the silver ion exchange material is selected from silver zirconium phosphate compounds, silver calcium phosphate compounds, silver zeolite compounds, silver glass compounds, and any combinations thereof.

4. The substrate of claim 3, wherein said silver ion exchange material is a silver zirconium phosphate compound.

5. The substrate of claim 1, wherein said substrate is a knit fabric.

6. The substrate of claim 1, wherein said substrate exhibits antimicrobial properties.

* * * * *